US012746244B2

(12) United States Patent
Cotter

(10) Patent No.: US 12,746,244 B2
(45) **Date of Patent: *Sep. 29, 2026**

(54) METHODS OF TREATING PRADER WILLI SYNDROME AND CONDITIONS ASSOCIATED WITH LOW BASAL METABOLIC RATE OR HYPERPHAGIA USING A $K_{ATP}$ CHANNEL OPENER

(71) Applicant: Sedogen LLC, Glenview, IL (US)

(72) Inventor: Sara Cotter, Wilmette, IL (US)

(73) Assignee: Sedogen LLC, Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/554,226

(22) Filed: Mar. 2, 2026

(65) Prior Publication Data

US 2026/0216203 A1 Jul. 30, 2026

Related U.S. Application Data

(63) Continuation of application No. 18/460,055, filed on Sep. 1, 2023, now Pat. No. 12,589,098, which is a continuation of application No. 17/093,251, filed on Nov. 9, 2020, now abandoned, which is a continuation of application No. 16/277,654, filed on Feb. 15, 2019, now abandoned, which is a continuation of application No. 14/849,679, filed on Sep. 10, 2015, now abandoned, which is a continuation of application No. 14/298,480, filed on Jun. 6, 2014, now abandoned.

(60) Provisional application No. 61/832,779, filed on Jun. 8, 2013.

(51) Int. Cl.

| | |
|---|---|
| ***A61K 31/549*** | (2006.01) |
| ***A61K 31/145*** | (2006.01) |
| ***A61K 31/19*** | (2006.01) |
| ***A61K 31/198*** | (2006.01) |
| ***A61K 31/522*** | (2006.01) |
| ***A61K 38/095*** | (2019.01) |
| ***A61K 38/27*** | (2006.01) |
| ***A61K 45/06*** | (2006.01) |

(52) U.S. Cl.

CPC .......... *A61K 31/549* (2013.01); *A61K 31/145* (2013.01); *A61K 31/19* (2013.01); *A61K 31/198* (2013.01); *A61K 31/522* (2013.01); *A61K 38/095* (2019.01); *A61K 38/27* (2013.01); *A61K 45/06* (2013.01)

(58) Field of Classification Search

CPC .... A61K 31/549; A61K 31/145; A61K 31/19; A61K 31/198; A61K 31/522; A61K 38/095; A61K 38/27; A61K 45/06

See application file for complete search history.

(56) References Cited

U.S. PATENT DOCUMENTS

| | | | | |
|---|---|---|---|---|
| 12,589,098 | B2 * | 3/2026 | Cotter | A61K 31/549 |
| 2006/0051418 | A1 | 3/2006 | Cowen et al. | |
| 2009/0062264 | A1 | 3/2009 | Cowen et al. | |
| 2009/0148526 | A1 | 6/2009 | Cowen et al. | |
| 2010/0016425 | A1 | 1/2010 | Vath | |

OTHER PUBLICATIONS

Alemzadeh et al., Beneficial effect of diazoxide in obese hyperinsulinemic adults. *J. Clin. Endocrinol. Metab.* 83(6): 1911-5 (1998).

Alemzadeh et al., Effect of diazoxide on brain capillary insulin receptor binding and food intake in hyperphagic obese Zucker rats. *Endocrinology*. 140(7): 3197-3202 (1999).

Amendment filed in U.S. Appl. No. 14/458,032 dated Oct. 3, 2016 (8 pages).

Declaration under 37 C.F.R. § 1.132 of Neil M. Cowen filed in U.S. Appl. No. 14/458,032 dated Aug. 25, 2015 (7 pages).

Declaration under 37 C.F.R. § 1.132 of Neil M. Cowen filed in U.S. Appl. No. 14/458,032 dated Sep. 30, 2016 (7 pages).

Dykens et al., Prader-Willi syndrome and autism spectrum disorders: an evolving story. *J. Neurodevelop. Disord.* 3: 225-37 (2011).

Dykens et al., Diagnoses and characteristics of autism spectrum disorders in children with Prader-Willi syndrome. *J. Neurodevelop. Disord.* 9: 1-12 (2017).

Lawson, Potassium channel openers as potential therapeutic weapons in ion channel disease. *Kidney Int.* 57: 838-45 (2000).

Lee, Disease management of Prader-Willi syndrome. *Expert Opin. Pharmacother*. 3(10): 1451-9 (2002).

Letter to the Editor, Prader-Willi and Bipolar Illness. *J. Am. Acad. Child Adolesc. Psychiatry*, 32:4 (1993).

Marijcke et al., Autism spectrum disorders in Prader-Willi and Angelman syndromes: a systematic review. *Psychiatr. Genet.* 15: 243-54 (2005).

Office Action issued in U.S. Appl. No. 14/458,032 dated Jun. 30, 2016 (12 pages).

Office Action issued in U.S. Appl. No. 14/458,022 dated Jan. 13, 2017 (15 pages).

Warnock et al., Onset of menses in two adult patients with Prader-Willi syndrome treated with fluoxetine. *Psychopharmacol. Bull.* 31(2): 239-42 (1995).

* cited by examiner

*Primary Examiner* — Olga N Chernyshev

(74) *Attorney, Agent, or Firm* — RinLaures LLC; Li-Hsien RinLaures; Kristen A. Dola

(57) ABSTRACT

This invention relates to treating Prader-Willi Syndrome (PWS) using a $K_{ATP}$ channel opener. The channel opener may be coadministered with other therapies used to treat PWS, such as human growth hormone, a wakefulness promoting agent, or a psychiatric or mood stabilizing drug, thereby allowing the baseline dosages of these other therapies to be decreased or making these other therapies unnecessary. The invention also relates to treating PWS based on the PWS nutritional phase of a patient, to prevent the patient's PWS nutritional phase from progressing or shift the patient's PWS nutritional phase back to an earlier phase. The invention further relates to treating PWS, and conditions associated with low basal metabolic rate or hyperphagia, with the $K_{ATP}$ channel opener based on a patient's blood ketone levels.

1 Claim, No Drawings

METHODS OF TREATING PRADER WILLI SYNDROME AND CONDITIONS ASSOCIATED WITH LOW BASAL METABOLIC RATE OR HYPERPHAGIA USING A $K_{ATP}$ CHANNEL OPENER

FIELD OF THE INVENTION

This invention relates to treating Prader-Willi Syndrome (PWS) and conditions affecting basal metabolic rate using a $K_{ATP}$ channel opener. The $K_{ATP}$ channel opener may be coadministered with other therapies used to treat PWS, such as human growth hormone, a wakefulness promoting agent, or a psychiatric/mood stabilizing medication, which may allow the dose of these other therapies to be reduced relative to the dose that would otherwise be given to a patient with PWS in the absence of the $K_{ATP}$ channel opener (e.g., baseline dose). The $K_{ATP}$ channel opener may also obviate the need for the use of the other therapies used to treat PWS, such that PWS may be treated without human growth hormone, a wakefulness promoting agent, or a psychiatric/mood stabilizing medication. The $K_{ATP}$ channel opener dosage may also be administered according to the PWS nutritional phase of a patient. The $K_{ATP}$ channel opener may also be administered to prevent the PWS patient's PWS nutritional phase from progressing, or to shift the PWS nutritional phase back to an earlier phase. The $K_{ATP}$ channel opener dosage for treating PWS or conditions associated with low basal metabolic rate or hyperphagia, such as obesity, may be modulated according to a patient's blood ketone level or diet.

BACKGROUND OF THE INVENTION

Prader-Willi syndrome (PWS) is a complex neurobehavioral disorder which is due to the absence of normally active paternally expressed genes from the chromosome 15q11-q13 region. PWS is an imprinted condition with 70-75% of the cases due to a de novo deletion in the paternally inherited chromosome 15 11-q13 region, 20-30% from maternal uniparental disomy 15 (UPD), and the remaining 2-5% from either microdeletions or epimutations of the imprinting center (i.e., imprinting defects). Clinical features of PWS include hypotonia and poor feeding in infancy which almost always requires some type of assisted feeding for a period of time, followed by hyperphagia as the child ages. Obesity typically begins around 2 years of age if the diet is not restricted. Behavioral problems and neuroendocrine abnormalities are also characteristic of PWS.

Given the complexity of PWS, its symptoms are treated with a number of different medications, including human growth hormone (GH), psychiatric/mood stabilizing medications, and wakefulness promoting agents. Many of the aforementioned drugs that are currently used to treat PWS have undesirable side effects. Accordingly, there is a need in the art to reduce these side effects by providing a way to reduce the dosages of the drugs used to treat PWS, or eliminate the need to use such drugs.

SUMMARY OF THE INVENTION

Provided herein is a method for treating Prader-Willi Syndrome, which may comprise administering a $K_{ATP}$ channel opener and a human growth hormone (GH) to a patient in need thereof. The dose of human growth hormone may be reduced in comparison to a baseline or adjusted GH dose. The baseline or adjusted GH dose may be reduced by at least 10, 20, 50, 80, 90, or 100%.

Further provided herein is a method for treating Prader-Willi Syndrome, which may comprise administering a $K_{ATP}$ channel opener and a psychiatric or mood stabilizing drug to a patient in need thereof. The dose of the psychiatric or mood stabilizing drug may be reduced in comparison to a baseline psychiatric or stabilizing drug dose. The baseline psychiatric medication dose may be reduced by at least 10, 20, 50, 80, 90, or 100%. The psychiatric or mood stabilizing drug may be a selective serotonin reuptake inhibitor (SSRI), a norepinephrine reuptake inhibitor (NRI), a noradrenergic and specific serotonergic antidepressant (NaSSA), a serotonin-norepinephrine reuptake inhibitor (SNRI), a serotonin antagonist and reuptake inhibitor (SARI), a norepinephrine-dopamine reuptake inhibitor, a selective serotonin reuptake enhancer, a norepinephrine-dopamine disinhibitor, a tricyclic antidepressant, a tetracyclic antidepressant, a monoamine oxidase inhibitor (MAOI), N-acetylcysteine, cysteamine, oxytocin, a mood stabilizer, an anticonvulsant, a metabotropic glutamate receptor modulator, a typical antipsychotic, or an atypical antipsychotic.

Also provided herein is a method for treating Prader-Willi Syndrome, which may comprise administering a $K_{ATP}$ channel opener and a wakefulness promoting agent to a patient in need thereof. The dose of the wakefulness promoting agent may be reduced in comparison to a baseline wakefulness promoting agent dose. The baseline wakefulness promoting agent dose may be reduced by at least 10, 20, 50, 80, 90, or 100%. The wakefulness promoting agent may be a stimulant, an amphetamine, a norepinephrine reuptake inhibitor (NRI), a norepinephrine-dopamine reuptake inhibitor (NDRI), a tricyclic antidepressant, a serotonin-norepinephrine reuptake inhibitor (SNRI), an H3-receptor antagonist, an orexin agonist, sodium oxybate, caffeine, or a eugeroic.

Further provided herein is a method for treating Prader-Willi Syndrome which may comprise administering a $K_{ATP}$ channel opener to a patient in need thereof. The patient may be in PWS nutritional phase 0, 1a, 1b, 2a, 2b, 3, or 4. The patient's PWS nutritional phase may be prevented from progressing to a later phase. The patient may be in PWS nutritional phase 1a, 1b, 2a, or 2b, and the patient's PWS nutritional phase may be prevented from progressing to phase 1b, 2a, 2b, or 3. The patient's PWS nutritional phase may be shifted back to an earlier PWS nutritional phase. The patient may be in PWS nutritional phase 3 or 4, and the patient's PWS nutritional phase may be shifted back to phase 1a, 1b, 2a, or 2b.

Also provided herein is a method for treating a disease or condition selected from Prader-Willi Syndrome, a condition associated with low basal metabolic rate, and a condition associated with hyperphagia. The method may comprise administering a $K_{ATP}$ channel opener to a patient in need thereof, and the patient's blood ketone level may be less than a target level selected from 3.0, 2.5, 2.0, 1.5, 1.0, 0.6, 0.5, 0.4, 0.3, 0.2, and 0.1 mmol/mL. The method may further comprise the step of administering a subsequent dose of the $K_{ATP}$ channel opener to the patient. The subsequent dose may be higher than the previous dose if the patient's blood ketone level is less than or equal to the target level after administration of the previous dose, and the subsequent dose may be equal to or less than the previous dose if the patient's blood ketone level is greater than or equal to the target level after administration of the previous dose.

Also provided herein is a method for treating autistic symptoms or behaviors associated with Prader-Willi Syndrome, which may comprise administering a $K_{ATP}$ channel opener to a patient in need thereof.

DETAILED DESCRIPTION

The inventor has made the surprising discovery that administering a $K_{ATP}$ channel opener (e.g., diazoxide) in combination with other therapies used to treat Prader-Willi Syndrome (PWS) allows the dosages of these other therapies to be reduced relative to the dosages that would ordinarily be administered in the absence of the $K_{ATP}$ channel opener, or to be entirely eliminated from a PWS treatment regimen. For example, various symptoms of PWS can be treated with human growth hormone, wakefulness promoting agents (e.g., modafinil), and psychiatric/mood stabilizing medications. The standard doses of such therapies are associated with undesirable side effects, such as insulin resistance in the case of growth hormone. Coadministering a $K_{ATP}$ channel opener allows lower doses of these other PWS therapies to be used, thereby resulting in fewer or reduced side effects. The inventor has also unexpectedly found that the efficacy of a $K_{ATP}$ channel opener is affected by the nutritional phase of a patient's PWS. Therefore, the $K_{ATP}$ channel opener may be administered according to the PWS nutritional phase of the patient, and may prevent the patient's PWS nutritional phase from progressing or shift the patient's PWS nutritional phase back to an earlier phase. Surprisingly, the inventor has also discovered that PWS and conditions associated with low basal metabolic rate or hyperphagia can be treated by modulating the dose of $K_{ATP}$ channel opener based on a patient's blood ketone level and/or diet.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Halo" and "halogen" refer to all halogens, that is, chloro (Cl), fluoro (F), bromo (Br), or iodo (I).

"Hydroxyl" and "hydroxy" means the group —OH.

"Substituted oxy" means the group —$OR^{aa}$, where $R^{aa}$ can be alkyl, substituted alkyl, acyl, substituted acyl, aryl, substituted aryl, heteroaryl, substituted heteroaryl, aralkyl, substituted aralkyl, cycloalkyl, substituted cycloalkyl, heterocyclyl, or substituted heterocyclyl.

"Substituted thiol" means the group —$SR^{bb}$, where $R^{bb}$ can be alkyl, substituted alkyl, acyl, substituted acyl, aryl, substituted aryl, heteroaryl, substituted heteroaryl, aralkyl, substituted aralkyl, cycloalkyl, substituted cycloalkyl, heterocyclyl, or substituted heterocyclyl.

"Alkyl" means an alkane-derived radical containing from 1 to 10, preferably 1 to 6, more preferably 1-4, yet more preferably 1-2, carbon atoms. Alkyl includes straight chain alkyl, branched alkyl and cycloalkyl, such as methyl, ethyl, propyl, isopropyl, butyl, t-butyl, and the like. The alkyl group can be attached at any available point to produce a stable compound. An "alkylene" is a divalent alkyl.

A "substituted alkyl" means an alkyl group independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, amino sulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound. In particular, "fluoro substituted" refers to substitution by 1 or more, e.g., 1, 2, or 3 fluorine atoms. "Optionally fluoro substituted" means that substitution, if present, is fluoro. The term "optionally substituted" as used herein means that substitution may, but need not, be present.

"Lower alkyl" means an alkyl group having 1-6 carbon atoms.

A "substituted lower alkyl" means a lower alkyl which is substituted with 1 or more, e.g., 1, 2, or 3, groups or substituents, as defined above, attached at any available point to produce a stable compound.

"Cycloalkyl" means saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like. "Cycloalkylene" is a divalent cyclo alkyl.

"Substituted cycloalkyl" means saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound.

"Aryl" alone or in combination means phenyl or naphthyl optionally carbocyclic fused with a cycloalkyl of preferably 5-7, more preferably 5-6, ring members.

"Substituted aryl" means an aryl group as defined above independently substituted with 1 or more, e.g., 1, 2, or 3, groups or substituents such as halo, hydroxy, optionally substituted alkoxy, optionally substituted alkylthio, alkylsulfinyl, alkylsulfonyl, optionally substituted amino, optionally substituted amido, amidino, urea optionally substituted with alkyl, aminosulfonyl optionally N-mono- or N,N-di-substituted with alkyl, alkylsulfonylamino, carboxyl, heterocycle, substituted heterocycle, nitro, cyano, thiol, sulfonylamino or the like attached at any available point to produce a stable compound.

"Alkoxy" means the group —$OR^{cc}$, where $R^{cc}$ is alkyl. "Lower alkoxy" denotes the group —$OR^{ccc}$, where $R^{ccc}$ is lower alkyl "Substituted alkoxy" means the group —$OR^{dd}$, where $R^{dd}$ is substituted alkyl. "Substituted lower alkoxy" means the group —$OR^{ddd}$, where $R^{ddd}$ is substituted lower alkyl.

"Alkylthio" or "thioalkoxy" means the group —S—$R^{ee}$, where $R^{ee}$ is alkyl.

"Substituted alkylthio" or "substituted thioalkoxy" means the group —S—R, where R is substituted alkyl.

"Sulfinyl" means the group —S(O)—.

"Sulfonyl" means the group —$S(O)_2$.

"Substituted sulfinyl" means the group —S(O)$R^{ff}$, where $R^{ff}$ is alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Substituted sulfonyl" means the group —S(O)$_2$$R^{gg}$, where $R^{gg}$ is alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl or substituted aralkyl.

"Sulfonylamino" means the group —S(O)$_2$N$R^{hh}$— where $R^{hh}$ is hydrogen or alkyl.

"Substituted sulfonylamino" means the group —S(O)$_2$N$R^{ii}$—$R^{ij}$, where $R^{ii}$ is hydrogen or optionally substituted alkyl, and $R^{ij}$ is alkyl, substituted alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl or substituted aralkyl.

"Amino" or "amine" means the group —$NH_2$. A "divalent amine" denotes the group —NH—. A "substituted divalent amine" denotes the group —N$R^{kk}$— wherein $R^{kk}$ is alkyl, substituted alkyl, aryl, substituted aryl, heteroaryl, substituted heteroaryl, acyl, substituted acyl, sulfonyl or substituted sulfonyl.

"Substituted amino" or "substituted amine" means the group —N$R^{mm}$$R^{nn}$, wherein $R^{mm}$ and $R^{nn}$ are independently hydrogen, alkyl, substituted alkyl, aryl, substituted aryl, heteroaryl, substituted heteroaryl, acyl, substituted acyl, sulfonyl, substituted sulfonyl, or cycloalkyl provided, however, that at least one of $R^{mm}$ and $R^{nn}$ is not hydrogen. $R^{mm}R^{nn}$ in combination with the nitrogen may form an optionally substituted heterocyclic or heteroaryl ring.

"Alkylsulfinyl" means the group —S(O)$R^{oo}$, wherein $R^{oo}$ is optionally substituted alkyl.

"Alkylsulfonyl" means the group —S(O)$_2$$R^{pp}$, wherein $R^{pp}$ is optionally substituted alkyl.

"Alkylsulfonylamino" means the group —N$R^{qq}$S(O)$_2$$R^{rr}$, wherein $R^{rr}$ is optionally substituted alkyl, and $R^{qq}$ is hydrogen or alkyl.

A "primary amino substituent" means the group —$NH_2$.

A "secondary amino substituent" means the group —NH$R^{ss}$, wherein $R^{ss}$ is alkyl, substituted alkyl, aryl, substituted aryl, heteroaryl, substituted heteroaryl, acyl, substituted acyl, sulfonyl, substituted sulfonyl, or cycloalkyl.

A "tertiary amino substituent" means the group —N$R^{ss}$$R^{tt}$, wherein $R^{ss}$ and $R^{tt}$ are independently alkyl, substituted alkyl, aryl, substituted aryl, heteroaryl, substituted heteroaryl, acyl, substituted acyl, sulfonyl, substituted sulfonyl, or cycloalkyl.

"Quaternary ammonium substituent" means the group —$N^+$$R^{ss}$$R^{tt}$$R^{uu}$, wherein $R^{ss}$, $R^{tt}$ and $R^{uu}$ are independently alkyl, substituted alkyl, aryl, substituted aryl, heteroaryl, substituted heteroaryl, acyl, substituted acyl, sulfonyl, substituted sulfonyl, or cycloalkyl.

"Heteroaryl" means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. "Heteroarylene" means a divalent heteroaryl.

"Heterocycle" or "heterocyclyl" means a saturated or unsaturated, non-aromatic carbocyclic group having a single ring or multiple condensed rings, e.g. a cycloalkyl group having from 5 to 10 atoms in which from 1 to 3 carbon atoms in a ring are replaced by heteroatoms, such as O, S, N, and are optionally fused with benzo or heteroaryl of 5-6 ring members and/or are optionally substituted. Heterocyclyl is intended to include oxidized S or N, such as sulfinyl, sulfonyl and N-oxide of a tertiary ring nitrogen. Examples of heterocycle or heterocyclyl groups are morpholino, tetrahydrofuranyl, dihydropyridinyl, piperidinyl, pyrrolidinyl, piperazinyl, dihydrobenzofuryl, dihydroindolyl, and the like.

"Heterocyclylalkyl" means the group —R-Het where Het is a heterocycle group and R is an alkylene group.

A "substituted heteroaryl," "substituted heterocyclyl," or "substituted heterocyclylalkyl" means a heteroaryl, heterocyclyl, or heterocyclylalkyl, respectively, independently substituted with 1 or more, e.g., 1, 2, or 3, groups or substituents such as halogen, hydroxy, optionally substituted alkoxy, optionally substituted alkylthio, alkylsulfinyl, alkylsulfonyl, acyloxy, optionally substituted aryl, optionally substituted aryloxy, optionally substituted heteroaryloxy, optionally substituted amino, optionally substituted amido, amidino, urea optionally substituted with alkyl, aryl, heteroaryl or heterocyclyl groups, amino sulfonyl optionally N-mono- or N,N-di-substituted with alkyl, aryl or hetero aryl groups, alkylsulfonylamino, arylsulfonylamino, heteroarylsulfonylamino, alkylcarbonylamino, arylcarbonylamino, heteroarylcarbonylamino, carboxyl, heterocycle, substituted heterocycle, heteroaryl, substituted heteroaryl, nitro, cyano, thiol, sulfonylamino, optionally substituted alkyl, optionally substituted alkenyl, or optionally substituted alkynyl, attached at any available point to produce a stable compound.

"Amido" means the group —C(O)$NH_2$. "Substituted amido" means the group —C(O)N$R^k$$R^l$, wherein $R^k$ and $R^l$ are independently hydrogen, lower alkyl, substituted lower alkyl, aryl, substituted aryl, heteroaryl, or substituted heteroaryl, provided, however, that at least one of $R^k$ and $R^l$ is not hydrogen. $R^kR^l$ in combination with the nitrogen may form an optionally substituted heterocyclic or heteroaryl ring.

"Amidino" means the group —C(═N$R^m$)N$R^n$$R^o$, wherein $R^m$, $R^n$, and $R^o$ are independently hydrogen or optionally substituted lower alkyl.

"Acyloxy" means the group —OC(O)$R^h$, where $R^h$ is hydrogen, alkyl, substituted alkyl, cyclo alkyl, substituted cycloalkyl, heterocyclyl, substituted heterocyclyl, aryl, substituted aryl, heteroaryl, substituted heteroaryl and the like.

"Aryloxy" means the group —OAr, where Ar is an aryl, or substituted aryl, group. "Heteroaryloxy" means groups —OHet, wherein Het is an optionally substituted heteroaryl group.

"Arylsulfonylamino" means the group —N$R^q$S(O)$_2$$R^s$, wherein $R^s$ is optionally substituted aryl, and $R^q$ is hydrogen or lower alkyl. "Heteroarylsulfonylamino" means the group —N$R^q$S(O)$_2$$R^t$, wherein $R^t$ is optionally substituted heteroaryl, and $R^q$ is hydrogen or lower alkyl.

"Alkylcarbonylamino" means the group —$NR^qC(O)R^p$, wherein $R^p$ is optionally substituted alkyl, and $R^q$ is hydrogen or lower alkyl.

"Arylcarbonylamino" means the group —$NR^qC(O)R^s$, wherein $R^s$ is optionally substituted aryl, and $R^q$ is hydrogen or lower alkyl.

"Heteroarylcarbonylamino" means the group —$NR^qC(O)R^t$, wherein $R^t$ is optionally substituted aryl, and $R^q$ is hydrogen or lower alkyl.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Method of Treating Prader-Willi Syndrome with a $K_{ATP}$ Channel Opener

Provided herein are methods of treating PWS by administering a $K_{ATP}$ channel opener to a patient. The $K_{ATP}$ channel opener may be used to treat obesity, prediabetes, diabetes, hypertension, depression, elevated cholesterol, other obesity associated co-morbidities, ischemic and reperfusion injury, epilepsy, cognitive impairment, schizophrenia, mania, other psychotic diseases, and the like. The $K_{ATP}$ channel opener may (a) inhibit fasting insulin secretion, (b) inhibit stimulated insulin secretion, (c) elevate energy expenditure, (d) elevate beta oxidation of fat, or (e) inhibit hyperphagia.

a. Combined Treatment with Reduced Dosage of Growth Hormone

The $K_{ATP}$ channel opener may be coadministered with a human growth hormone (GH) to treat PWS. The combination therapy may be used to improve body composition abnormalities and improve linear growth of an infant or child with PWS, or to improve body composition abnormalities in an adult with PWS. The combination therapy may also be used to improve lean body mass, decrease body fat, modulate bone mineral density, or normalize adult height. The therapy may also be used to improve cognition, tone, endurance, stamina, strength, agility, or motor development, or to positively affect nitrogen balance or increase energy expenditure.

The GH dose may be 0.18-0.3 mg/kg/week, and may be administered as a daily subcutaneous injection. The baseline GH dose may also be at least 0.01, 0.05, 0.1, 0.15, 0.2, 0.3, 0.4, 0.5, 1.0, 1.5, or 2.0 mg/kg/week. The baseline GH dose may also be less than 0.01, 0.05, 0.1, 0.15, 0.2, 0.3, 0.4, 0.5, 1.0, 1.5, or 2.0 mg/kg/week. The GH dose may be adjusted based on the weight of the patient. The dose may also be adjusted based on the patient's lean mass or on insulin growth factor (IGF-1) levels, such that the IGF-1 levels do not exceed 3 standard deviations above the upper limit of normal. The upper limit of normal for IGF-1 levels may be 25-1000 ng/mL, and may be in a range as described in Table 1.

TABLE 1

IGF-1 Reference Levels

| Age | Male (ng/mL) | Female (ng/mL) |
|---|---|---|
| Adult | | |
| 19-30 y | 126-382 | 138-410 |
| 31-40 y | 106-255 | 126-291 |
| 41-50 y | 86-220 | 88-249 |
| 51-60 y | 87-225 | 92-190 |
| 61-70 y | 75-228 | 87-178 |
| 71-80 y | 31-187 | 25-171 |
| 81-88 y | 68-157 | 31-162 |
| Children | | |
| 1-7 d | ≤31 | ≤31 |
| 8-14 d | ≤43 | ≤43 |
| 15 d-1 y | 25-265 | 25-265 |
| 1-2 y | 45-222 | 99-254 |
| 3-4 y | 36-202 | 36-202 |
| 5-6 y | 32-259 | 57-260 |
| 7-8 y | 65-278 | 97-352 |
| 9-10 y | 52-330 | 49-461 |
| 11-12 y | 80-723 | 101-580 |
| 13-14 y | 142-855 | 199-658 |
| 15-16 y | 176-845 | 236-808 |
| 17-18 y | 152-668 | 165-526 |

When administered together with the $K_{ATP}$ channel opener, the dose of GH may be reduced as compared to the baseline dose of GH. The reduction may be by at least 10, 20, 50, 80, or 90% of the baseline or adjusted GH dose. The GH dosage may also be reduced by decreasing the frequency of GH administration, such that GH is administered 6, 5, 4, 3, 2, or 1 time(s) per week. The reduction in GH dose may decrease the side effects or risks of GH, such as the induction of insulin resistance or diabetes mellitus, acromegaly, scoliosis, intracranial hypertension, neoplasm or death. PWS may also be treated by administering the $K_{ATP}$ channel opener in the absence of GH.

The $K_{ATP}$ channel opener may also be used to treat an adult patient with PWS. The adult may be greater than or equal to 18 years of age. The $K_{ATP}$ channel opener may normalize IGF-1 levels in the adult. Accordingly the adult may be treated with the $K_{ATP}$ channel opener without having to use GH, or by using a lower dose of GH than the baseline dose.

(1) Treatment Based on IGF-1 Levels

IGF-1 levels may be indicative of the levels of GH. Administering the $K_{ATP}$ channel opener may allow a lower dose of GH to be administered in combination with the $K_{ATP}$ channel opener. This may be due to an increase IGF-1 levels mediated by the channel opener in patients with PWS. Accordingly, the dosage of the $K_{ATP}$ channel opener may be based on IGF-1 levels, such that the IGF-1 levels do not exceed 3 standard deviations above the upper limit of normal. The upper limit of normal for IGF-1 levels may be 25-1000 ng/mL, and may be in a range as described in Table 1.

b. Combined Treatment with Reduced Dosage of Psychiatric or Mood Stabilizing Drugs The $K_{ATP}$ channel opener may be coadministered with a psychiatric or mood stabilizing drug, such as a psychotropic medication, to treat PWS by treating a PWS behavioral symptom. The PWS behavioral symptom may be obsessions, compulsions, addiction, autism or autistic tendencies, anxiety, depression, mood swings, skin picking or psychotic behavior. The psychotropic medication may be a selective serotonin reuptake inhibitor (SSRI), norepinephrine reuptake inhibitor (NRI), noradrenergic and specific serotonergic antidepressant (NaSSA), serotonin-norepinephrine reuptake inhibitor (SNRI), serotonin antagonist and reuptake inhibitor (SARI), norepinephrine-dopamine reuptake inhibitor, selective serotonin reuptake enhancer, norepinephrine-dopamine disinhibitor, tricyclic antidepressant, tetracyclic antidepressant, monoamine oxidase inhibitor (MAOI), N-acetylcysteine, cysteamine, oxytocin, mood stabilizer, anticonvulsant, metabotropic glutamate receptor modulator, typical antipsychotic, or atypical antipsychotic. The SSRI may be citalopram, dapoxetine, escitalopram, fluoxetine, fluvoxamine, paroxetine, or sertraline. The NRI may be atomoxetine, bupropion, reboxetine, edivoxetine, tapentadol or viloxazine. The NaSSA may be mianserin or mirtazapine. The SNRI may be desvenlafaxine, duloxetine, milnacipran, or venlafaxine. The SARI may be etoperidone, nefazodone, or trazdone. The norepinephrine-dopamine reuptake inhibitor may be bupropion. The selective serotonin reuptake enhancer may be tianeptine or amineptine. The norepinephrine-dopamine disinhibitor may be agomelatine. The tricyclic antidepressant may be amitriptyline, amitriptylinoxide, clomipramine, butriptyline, clomipramine, demexiptiline, desipramine, dibenzepin, dimetacrine, dosulepin, doxepin, imipramine, imipraminoxide, lofepramine, imipraminozide, lofepramine, melitracen, metapramine, nitroxazepine, nortriptyline, noxiptiline, pipofezine, propizepine, protriptyline, quinupramine, amineptine, iprindole, opipramol, tianeptine, or trimipramine. The tetracyclic antidepressant may be amoxapine, maprotiline, mazindol, mianserin, mirtazapine, or setiptiline. The MAOI may be isocarboxazid, phenelzine, selgiline, tranylcypromine, moclobemide, or pirlindole. The mood stabilizer may be lithium or an anticonvulsant such as valproic acid, divalproex sodium, sodium valproate, lamotrigine, oxcarbazepine, topiramate, riluzole, gabapentin, pregabalin, carbamazepine, vigabatrin, progabide, tiagabine, zonisamide, or phenytoin. The metabotropic glutamate receptor modulator may be fenobam, mavoglurant, GRN-529, STX107, STX110, RO4917523, dipraglurant, ADX-71149/JNJ-40411813, RO4491533, or RO4995819. The typical antipsychotic may be haloperidol, droperidol, chlorpromazine, fluphenazine, perphenazine, prochlorperazine, thioridazine, trifluorperazine, mesoridazine, periciazine, promazine, triflupromazine, levomepromazine, promethazine, pimozide, cyamemazine, chlorprothixene, clopenthixol, flupenthixol, thiothixene, or zuclopenthixol. The atypical antipsychotic may be amisulpride, aripiprazole, asenapine, blonanserin, carpipramine, clocapramine, clotiapine, clozapine, iloperidone, lurasidone, mosapramine, olanzapine, paliperidone, perospirone, quetiapine, remoxipride, risperidone, sertindole, sulpiride, ziprasidone, zotepine, bitopertin (RG1678), cariprazine (RGH-188), LY2140023, pimavanserin (ACP-103), vabicaserin (SCA-136), or zicronapine (Lu 31-130). The baseline psychiatric drug dose may be at least 1, 5, 10, 15, 20, 30, 40, 50, 100, 200, 300, 400, 500, 1000, or 2000 mg. The dose may also be less than 1, 5, 10, 15, 20, 30, 40, 50, 100, 200, 300, 400, 500, 1000, or 2000 mg. The psychiatric drug may be administered once, twice, three times, four times, five times, seven times, eight times, nine times, ten times, eleven times, or twelve times daily. The psychiatric drug may also be administered once every 1, 2, 3, 4, or 5 weeks.

When administered together with the $K_{ATP}$ channel opener, the dose of the psychiatric medication may be by at least 10, 20, 50, 80, or 90% of the baseline psychiatric medication dose. The frequency of administering the psychiatric medication dosage may also be decreased if the psychiatric medication is coadministered with the $K_{ATP}$ channel opener. The decrease may be by once, twice, three times, four times, five times, seven times, eight times, nine times, ten times, eleven times, or twelve times daily; or once twice, three times, four times, or five times per month. PWS may also be treated by administering the $K_{ATP}$ channel opener in the absence of the psychiatric medication.

c. Combined Treatment with Reduced Dosage of Wakefulness Promoting Agents

The $K_{ATP}$ channel opener may be coadministered with a wakefulness promoting agent to treat PWS. The PWS symptom being treated may be excessive daytime sleepiness, sleep apnea, narcolepsy (with or without cataplexy), cataplexy, hypnagogic hallucinations, hypnopompic hallucinations, or sleep paralysis. The wakefulness promoting agent may be a stimulant such as an amphetamine, a norepinephrine reuptake inhibitor (NRI), norepinephrine-dopamine reuptake inhibitor (NDRI), a tricyclic antidepressant, a serotonin-norepinephrine reuptake inhibitor (SNRI), an H3-receptor antagonist, an orexin agonist, sodium oxybate, caffeine, or a eugeroic (e.g., modanafil, adrafinil, armodafinil). The amphetamine may be dextroamphetamine, methamphetamine, mixed amphetamine salts (ADDERALL®), or lisdexamfetamine. The NRI may be atomoxetine, bupropion, reboxetine, edivoxetine, tapentadol or viloxazine. The NDRI may be dexmethylphenidate, fencamine, fencamfamine, or methylphenidate. The tricyclic antidepressant may be amitriptyline, amitriptylinoxide, clomipramine, butriptyline, clomipramine, demexiptiline, desipramine, dibenzepin, dimetacrine, dosulepin, doxepin, imipramine, imipraminoxide, lofepramine, imipraminozide, lofepramine, melitracen, metapramine, nitroxazepine, nortriptyline, noxiptiline, pipofezine, propizepine, protriptyline, quinupramine, amineptine, iprindole, opipramol, tianeptine, or trimipramine. The SNRI may be desvenlafaxine, duloxetine, milnacipran, or venlafaxine. The baseline wakefulness promoting agent dose may be at least 1, 5, 10, 15, 20, 30, 40, 50, 100, 200, 300, 400, 500, 1000, or 2000 mg. The dose may also be less than 1, 5, 10, 15, 20, 30, 40, 50, 100, 200, 300, 400, 500, 1000, or 2000 mg. The wakefulness promoting agent may be administered once, twice, three times, four times, five times, seven times, eight times, nine times, ten times, eleven times, or twelve times daily. The wakefulness promoting agent may also be administered once every 1, 2, 3, 4, or 5 weeks.

When administered together with the $K_{ATP}$ channel opener, the dose of the wakefulness promoting agent may be reduced as compared to the baseline dose of the wakefulness promoting agent. The reduction may be by at least 10, 20, 50, 80, or 90% of the wakefulness promoting agent dose. The frequency of administering the wakefulness promoting agent dosage may also be decreased if the wakefulness promoting agent is coadministered with the $K_{ATP}$ channel opener. The decrease may be by once, twice, three times, four times, five times, seven times, eight times, nine times, ten times, eleven times, or twelve times daily; or once twice, three times, four times, or five times per month. PWS may also be treated by administering the $K_{ATP}$ channel opener in the absence of the wakefulness promoting agent.

d. Treatment Based on Nutritional Phase

The $K_{ATP}$ channel opener may be administered based on the PWS nutritional phase of the patient. The nutritional phase may be as described in Table 2.

TABLE 2

| PWS Nutritional Phase | |
|---|---|
| Phase | Clinical Characteristics |
| Phase 0: Decreased fetal movements and lower birth weight | Full-term birth weight and BMI are about 15-20% less than the siblings<br>Typically normal gestational age<br>85% have decreased fetal movements |
| Phase 1a: Hypotonia with difficulty feeding (0-9 months) | Weak, uncoordinated suck. Usually cannot breastfeed<br>Needs assistance with feeding either through feeding tubes (nasal/oral gastric tube or gastrostomy tube) or orally with special, widened nipples. Many would die without assisted feeding<br>Oral feeds are very slow<br>Severely decreased appetite. Shows little or no evidence of being hungry<br>Does not cry for food or get excited at feeding time<br>If feeding just occurred when baby "acted hungry" then would have severe "failure-to-thrive"<br>Weak cry |
| Phase 1b: No difficulty feeding and growing appropriately on growth curve (9-25 months) | No longer needs assisted feeding<br>Growing steadily along growth curve with normal feeding<br>Normal appetite |
| Phase 2a: Weight increasing without an increase in appetite or excessive calories (2.1-4.5 years) | Infant starts crossing growth curve centile lines<br>No increase in appetite<br>Appetite appropriate for age<br>Will become obese if given the recommended daily allowance (RDA) for calories or if eating a "typical" toddler diet of 70% carbohydrates<br>Typically needs to be restricted to 60-80% of RDA to prevent obesity |
| Phase 2b: Weight increasing with an increase in appetite (4.5-8 years) | Increased interest in food. Frequently asking "food related" questions<br>Preoccupied with food. Very concerned about the next meal/snack (e.g., "Did you remember to pack my lunch?")<br>Increased appetite<br>Will eat more food than a typical child if allowed<br>Will eat food within their line of sight if unattended<br>Will become obese if allowed to eat what they want<br>Can be fairly easily redirected about food<br>Can feel full<br>Will stop eating voluntarily |
| Phase 3: Hyperphagic, rarely feels full (8 years to adulthood) | Constantly thinking about food<br>While eating one meal they are already thinking about the next meal<br>Will awaken from sleep early thinking about food<br>Will continue eating if portion size is not limited<br>Rarely (truly) feels full<br>Will steal food or money to pay for food<br>Can eat food from garbage and other unsavory/inedible sources (e.g., dog food, frozen food, crayons, etc.)<br>Typically are not truthful about what they have eaten (i.e. amount and types of food)<br>Will gain considerable amount of weight over a short period of time if not supervised (e.g., some individuals are known to have gained up to 20 pounds in one weekend)<br>Food typically needs to be locked up. Frequently the child will ask the parent to lock the food if the parent has forgotten<br>Will break into neighbors' houses for food<br>Temper tantrums and "meltdowns" frequently related to food<br>Needs to be placed on a diet that is approximately 50-70% of the RDA to maintain a healthy weight |
| Phase 4: Appetite is no longer insatiable (adulthood) | Appetite may still be increased or may be normal or less than normal<br>Previously in phase 3, but now a noticeable improvement in their appetite control<br>Can feel full<br>Appetite can fluctuate in this phase, but the key component is noticeable improvement in control of appetite compared to when they were younger<br>Not as preoccupied with food<br>Absence of major temper tantrums and "meltdowns" related to food<br>Onset in adulthood. Could be as early as 20s or as late as 40-50s |

The dose of the $K_{ATP}$ channel opener may also be adjusted according to the PWS nutritional phase of the patient.

The $K_{ATP}$ channel opener may also be administered to prevent the progression of a patient's PWS nutritional phase to a later phase. The $K_{ATP}$ channel opener may be administered to a PWS patient in PWS nutritional phase 1a or 1b, and may prevent the patient's PWS nutritional phase from progressing to phase 2a or 2b. In addition, the $K_{ATP}$ channel opener may be administered to a PWS patient in PWS nutritional phase 2a or 2b, and may prevent the PWS patient's nutritional phase from progressing to phase 3 or 4.

The $K_{ATP}$ channel opener may also be administered to shift a PWS patient's PWS nutritional phase back to an earlier phase. The $K_{ATP}$ channel opener may be administered to a PWS patient in PWS nutritional phase 3 or 4, and may shift the patient's PWS nutritional phase back to phase 1a, 1b, 2a, or 2b. The $K_{ATP}$ channel opener may also be administered to a PWS patient in PWS nutritional phase 2a or 2b, and may shift the patient's PWS nutritional phase back to phase 1a or 1b.

The $K_{ATP}$ channel opener dose administered to shift a patient's PWS nutritional phase or prevent a patient's PWS nutritional phase from advancing may be higher for a later PWS nutritional phase than the dose administered for an earlier PWS nutritional phase. The dose for the later PWS nutritional phase may be 10, 20, 40, 50, 60 or 80% higher, or may be 2, 3, 4, 5, 6, 7, 8, 9, or 10 times higher.

e. Treating Autism Symptoms Associated with PWS

The $K_{ATP}$ channel opener may be used to treat an autism-related symptom or an autism spectrum disorder (ASD) associated with PWS. The patient may have an elevated score on the Pervasive Developmental Disorder-Mental Retardation questionnaire that is indicative of an ASD. The patient may meet the criteria for an ASD on the Autism Diagnostic Observation Schedule or the Autism Diagnostic Interview, Revised. The patient may have a symptom such as an impairment in social interaction, language or communication; restricted, repetitive, or stereotyped behavior; stereotypies; a pronounced repetitive or compulsive behavior; skin picking; a need to tell, ask, or say; hoarding; ordering, arranging; symmetry or exactness; ritualized eating; rereading and rewriting; fearful of losing things; repeated checking; touching, tapping and rubbing; excessive washing; rectal picking; repetition of routines; or pulling hair out.

3. Method of Treating Prader-Willi Syndrome and Conditions Associated with Low Basal Metabolic Rate or Hyperphagia Based on Blood Ketone Levels Provided herein is a method of treating PWS or conditions associated with low basal metabolic rate or hyperphagia by administering the $K_{ATP}$ channel to a patient. The condition may be obesity. The $K_{ATP}$ channel opener may be administered according to a PWS patient's blood ketone level. The patient's blood ketone level may be less than or equal to a target level of 3.0, 2.5, 2.0, 1.5, 1.0, 0.6, 0.5, 0.4, 0.3, 0.2, or 0.1 mmol/L. The patient's target level may also be 0.6-1.5 mmol/L, 1.6-3.0 mmol/L, less than or equal to 1.4, 1.5 or 1.6 mmol/L, or greater than or equal to 1.5 mmol/L or 3.0 mmol/L. The dose of the $K_{ATP}$ channel opener may be increased for the patient in comparison to the patient's previous dose until the patient's blood ketone level is at least at the target level. The dose of the $K_{ATP}$ channel opener being administered to the patient may be maintained if the patient's blood ketone level is at the target level. The dose of the $K_{ATP}$ administered to the patient may be decreased in comparison to the patient's previous dose until the patient's blood ketone level is less than or equal to the target level. The dose of the $K_{ATP}$ channel opener may also be decreased in the event that the patient experiences an undesirable side effect, such as hyperglycemia.

4. $K_{ATP}$ Channel Opener

The $K_{ATP}$ channel opener may have the structure of one of Formula I-VIII.

Formula I

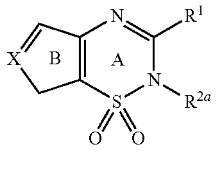

In Formula I,

R1 may be hydrogen, lower alkyl, substituted lower alkyl, cycloalkyl, or substituted cycloalkyl, provided however that when R1 is a substituted lower alkyl or a substituted cycloalkyl, then the substituent may not include an amino group;

R2a may be hydrogen;

X may be a 1, 2 or 3 atom chain, in which each atom is independently halogen, hydroxyl, lower alkyl, substituted lower alkyl, lower alkoxy, cycloalkyl, substituted cycloalkyl, or substituted lower alkoxy, provided however that when an atom of the chain is substituted with substituted lower alkyl, substituted lower alkoxy or substituted cycloalkyl, then the substituent may not include an amino group; and ring B may be saturated, monounsaturated, polyunsaturated or aromatic.

In Formula I, X may also be C(Ra)C(Rb), and Ra and Rb may be independently hydrogen, halogen, lower alkyl, substituted lower alkyl, cycloalkyl, substituted cycloalkyl, lower alkoxy, substituted lower alkoxy, sulfonyl, or the like. Ra and Rb may also be independently selected from hydroxyl, substituted oxy, substituted thiol, alkylthio, substituted alkylthio, sulfinyl, sulfonyl, substituted sulfinyl, substituted sulfonylalkylsulfinyl, alkylsulfonyl, and the like. Ring B may not include any heteroatoms.

Salts of the channel openers defined by Formula I may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

Formula II

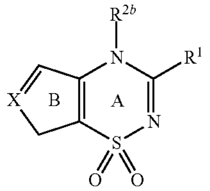

In Formula II,

R1 may be hydrogen, lower alkyl, substituted lower alkyl, cycloalkyl, or substituted cycloalkyl, provided however that when R1 is a substituted lower alkyl or a substituted cycloalkyl, then the substituent may not include an amino group;

R2b may be hydrogen;

X may be a 1, 2 or 3 atom chain, in which each atom is independently carbon, sulfur or nitrogen, and each atom may be optionally substituted with halogen, hydroxyl, lower alkyl, substituted lower alkyl, lower alkoxy, cycloalkyl, substituted cycloalkyl, or substituted lower alkoxy, provided however that when an atom of the chain is substituted with substituted lower alkyl, substituted cycloalkyl or substituted lower alkoxy, then the substituent may not include an amino group; and ring B may be saturated, monounsaturated, polyunsaturated or aromatic.

In Formula II, X may also be C(Ra)C(Rb), in which Ra and Rb are independently hydrogen, halogen, lower alkyl, substituted lower alkyl, cycloalkyl, substituted cycloalkyl, lower alkoxy, substituted lower alkoxy, sulfonyl, or the like. Ra and Rb may also be independently hydroxyl, substituted oxy, substituted thiol, alkylthio, substituted alkylthio, sulfinyl, sulfonyl, substituted sulfinyl, substituted sulfonyl, alkylsulfinyl, alkylsulfonyl, nitro or the like. Ring B may not include any heteroatoms.

Salts of the channel openers defined by Formula II may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

Formula III

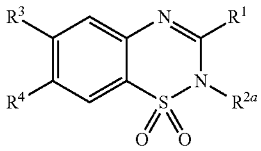

In Formula III,

R1 may be hydrogen, lower alkyl, substituted lower alkyl, or cycloalkyl, provided however that when R1 is a substituted lower alkyl, then the substituent may not include an amino group;

R2a may be hydrogen;

R3 may be hydrogen, halogen, lower alkyl, substituted lower alkyl, cycloalkyl or substituted cycloalkyl, provided however that when R3 is a substituted lower alkyl, then the substituent may not include an amino group; and R4 may be hydrogen, halogen, lower alkyl, substituted lower alkyl, cycloalkyl or substituted cycloalkyl, provided however that when R4 is a substituted lower alkyl, then the substituent may not include an amino group In Formula III, R1 may also be a lower alkyl, (ethyl or methyl); R2a may be hydrogen; and R3 and R4 may each independently be halogen.

In Formula III, R1 may also be methyl; R2a may be hydrogen; R3 may be hydrogen, halogen, lower alkyl, substituted lower alkyl, cycloalkyl, or substituted cycloalkyl; and R4 may be chlorine.

Salts of the channel openers defined by Formula III may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

Formula IV

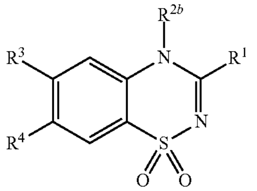

In Formula IV,

R1 may be hydrogen, lower alkyl, substituted lower alkyl, or cycloalkyl, provided however that when R1 is a substituted lower alkyl, then the substituent may not include an amino group;

R2b may be hydrogen;

R3 may be hydrogen, halogen, lower alkyl, substituted lower alkyl, cycloalkyl or substituted cycloalkyl, provided however that when R3 is a substituted lower alkyl, then the substituent may not include an amino group; and R4 may be hydrogen, halogen, lower alkyl, substituted lower alkyl, cycloalkyl or substituted cycloalkyl, provided however that when R4 is a substituted lower alkyl, then the substituent may not include an amino group.

In Formula IV, R1 may also be a lower alkyl, (ethyl or methyl); R2b may be hydrogen; and R3 and R4 may each independently be halogen.

In Formula IV, R1 may also be methyl; R2b may be hydrogen; R3 may be hydrogen, halogen, lower alkyl, substituted lower alkyl, cycloalkyl, or substituted cycloalkyl; and R4 may be chlorine.

Salts of the channel openers defined by Formula IV may be prepared from the following: (a) metal hydroxides, preferably alkali metal hydroxides (e.g., NaOH and KOH) and (b) organic hydroxides, preferably organic compounds which include at least one tertiary amine or at least one quaternary ammonium ion (e.g., diethylamine ethanol, triethylamine, hydroxyethylpyrrolidine, choline and hexamethylhexamethylenediammonium, and the like).

Formula V

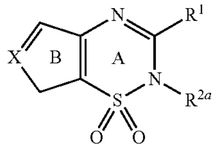

In Formula V,

R1 may be optionally substituted amino, optionally substituted alkyl, optionally substituted cycloalkyl, optionally substituted heterocyclyl, optionally substituted heterocyclylalkyl, optionally substituted aryl, optionally substituted heteroaryl, or optionally substituted heteroarylalkyl;

R2a may be hydrogen, and lower alkyl;

X may be a 1, 2 or 3 atom chain, in which each atom is independently carbon, sulfur or nitrogen, and each atom may be optionally substituted with halogen, hydroxyl, optionally substituted lower alkyl, optionally substituted lower alkoxy, optionally substituted cycloalkyl, or optionally substituted amino;

ring B may be saturated, monounsaturated, polyunsaturated or aromatic; and at least one of R1 or a substituent of X may include an amino group.

In Formula V, X may be C(Ra)C(Rb), in which Ra and Rb may be independently hydrogen, halogen, optionally substituted lower alkyl, optionally substituted cycloalkyl, optionally substituted lower alkoxy, amino, sulfonylamino, aminosulfonyl, sulfonyl, or the like. R1 may also include at least one substituent containing an amino group. Ra and Rb may be independently hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, or the like. Ring B may not include any heteroatoms.

Formula VI

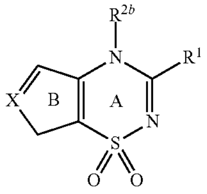

In Formula VI,

R1 may be optionally substituted amino, optionally substituted alkyl, optionally substituted cycloalkyl, optionally substituted heterocyclyl, optionally substituted heterocyclylalkyl, optionally substituted aryl, optionally substituted heteroaryl, or optionally substituted heteroarylalkyl;

R2b may be hydrogen or lower alkyl;

X may be a 1, 2 or 3 atom chain, in which each atom is independently carbon, sulfur or nitrogen, and each atom may be optionally substituted with halogen, hydroxyl, optionally substituted lower alkyl, optionally substituted lower alkoxy, optionally substituted cycloalkyl, or optionally substituted amino;

ring B may be saturated, monounsaturated, polyunsaturated or aromatic; and at least one of R1 or a substituent of X may include an amino group.

In Formula VI, X may also be C(Ra)C(Rb), in which Ra and Rb may be independently hydrogen, halogen, lower alkyl, substituted lower alkyl, cycloalkyl, substituted cycloalkyl, lower alkoxy, substituted lower alkoxy, amino, sulfonylamino, amino sulfonyl, sulfonyl, or the like. Ra and Rb may be independently hydroxyl, substituted oxy, substituted thiol, alkylthio, substituted alkylthio, sulfinyl, sulfonyl, substituted sulfinyl, substituted sulfonyl, substituted sulfonylamino, substituted amino, substituted amine, alkylsulfinyl, alkylsulfonyl, alkylsulfonylamino, or the like. R1 may include at least one substituent containing an amino group. Ring B may not include any heteroatoms.

Formula VII

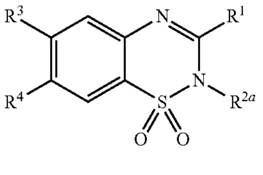

In Formula VII,

R1 may be optionally substituted amino, optionally substituted alkyl, optionally substituted cycloalkyl, optionally substituted heterocyclyl, optionally substituted heterocyclylalkyl, optionally substituted aryl, optionally substituted heteroaryl, or optionally substituted heteroarylalkyl;

R2a may be hydrogen, lower alkyl, or substituted lower alkyl;

R3 may be hydrogen, halogen, optionally substituted lower alkyl, optionally substituted amino, optionally substituted cycloalkyl or optionally substituted aryl;

R4 may be hydrogen, halogen, optionally substituted lower alkyl, optionally substituted amino, optionally substituted cycloalkyl or optionally substituted aryl; and at least one of R1, R3 and R4 may include a substituent containing an amino group.

Preferably, R1 includes a substituent containing an amino group. In particular embodiments of Formula VII; R1 includes an amino substituent, R2a is hydrogen; and R3 and R4 are each independently halogen.

In Formula VII, R2a may be hydrogen; R3 may be hydrogen, halogen, lower alkyl, substituted lower alkyl, amino, substituted amino, cycloalkyl, or substituted cycloalkyl; and R4 may be chlorine.

Formula VIII

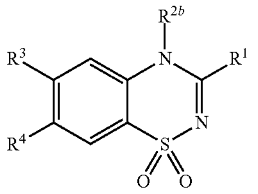

In Formula VIII,

R1 may be optionally substituted amino, optionally substituted alkyl, optionally substituted cycloalkyl, optionally substituted heterocyclyl, optionally substituted heterocyclylalkyl, optionally substituted aryl, optionally substituted heteroaryl, or optionally substituted heteroarylalkyl;

R2b may be hydrogen, lower alkyl, or substituted lower alkyl;

R3 may be hydrogen, halogen, optionally substituted lower alkyl, optionally substituted amino, optionally substituted cycloalkyl or optionally substituted aryl;

R4 may be hydrogen, halogen, optionally substituted lower alkyl, optionally substituted amino, optionally substituted cycloalkyl or optionally substituted aryl; and at least one of R1, R3 and R4 may include a substituent containing an amino group.

R1 may include a substituent containing an amino group. R2b may be hydrogen; and R3 and R4 may each independently be halogen.

In Formula VIII, R2b may also be hydrogen; R3 may be hydrogen, halogen, lower alkyl, optionally substituted lower alkyl, optionally substituted amino, or optionally substituted cycloalkyl; and R4 may be chlorine.

The $K_{ATP}$ channel opener may also have the formula 7-chloro-3-methyl-2-H-1,2,4-benzothiadiazine 1,1 dioxide (shown below with its tautomer) with the empirical formula C8H7ClN2O2S and a molecular weight of 230.7.

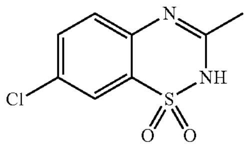

or

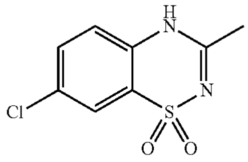

The $K_{ATP}$ channel opener may also be a salt of one of the compounds described by Formulae I-VIII and may have at least one, of the following properties: (1) opening SURx/

Kir6.y potassium channels, in which x=1, 2A or 2B and y=1 or 2; (2) binding to the SURx subunit of $K_{ATP}$ channels; and (3) inhibiting glucose induced release of insulin following administration of the compound in vivo.

The $K_{ATP}$ channel opener may also be a structural variant or bioequivalent of a compound defined by Formulae I-VIII, such as a derivative, salt, prodrug or isomer thereof. The salt of $K_{ATP}$ channel opener may have a cation that is a cation of an alkali metal or an organic compound which includes a tertiary amine or a quaternary ammonium ion. If the salt includes an anion of diazoxide and a sodium cation, then the salt may not be in a form suitable for intravenous use. If the anion is diazoxide in a solution suitable for intravenous use, then the cation may not be sodium. In solutions suitable for intravenous use, if the cation is sodium, then the anion may not be an anion of diazoxide. If the salt includes an anion of diazoxide and a sodium cation, then the salt may not be in liquid form. The $K_{ATP}$ channel opener may be a salt of a compound of one of Formulae I-VIII in which the cation is sodium, potassium, choline or hexamethyl hexamethylene diammonium. The $K_{ATP}$ channel opener may also be BPDZ 62, BPDZ 73, NN414, or BPDZ 154. For salts of compounds of Formula V-VIII, at least one substituent of the compound of Formulae V-VIII may include an amino group. The compound of Formula V-VIII may form an anion of a salt and a monovalent or divalent metal may form the cation. The cation may include a tertiary amino or quaternary ammonium group.

a. Dosage

The dose of the $K_{ATP}$ channel opener may be at least 1, 5, 10, 15, 20, 30, 40, 50, 100, 200, 300, 400, 500, 1000, or 2000 mg. The dose may also be less than 1, 5, 10, 15, 20, 30, 40, 50, 100, 200, 300, 400, 500, 1000, or 2000 mg. The dose may further be determined based on the weight of the subject for which it is to be administered, such that the formulation may contain a single administration dose of at least 0.1, 0.5, 1.0, 2.0, 3.0, 5.0, 10.0, or 20.0 mg per kg of the subject's body weight. The formulation may also contain a single administration dose of less than 0.1, 0.5, 1.0, 2.0, 3.0, 5.0, 10.0, or 20.0 mg per kg of the subject's body weight.

The efficacy of the $K_{ATP}$ channel opener may be enhanced or reduced by the composition of the patient's diet. Diets high in carbohydrates (e.g., >40% of calories from carbohydrates) may require higher doses of diazoxide to achieve optimal results. In contrast, a patient consuming a higher protein content diet (e.g. >15% of calories from protein) or higher fat content (e.g., >30% of calories from fat) may require lower doses of diazoxide to achieve optimal results. The variability in patients' diets and the impact of dietary composition on the drug's efficacy also lends itself to using a biomarker like blood ketone levels to monitor or titrate the patient's dose of diazoxide.

b. Compositions

This invention also relates to a method of treatment comprising administering a composition comprising a $K_{ATP}$ channel opener, which may be a therapeutically effective amount. The composition may be a pharmaceutical composition, which may be produced using methods well known in the art.

c. Administration

Administration of the composition using the method described herein may be orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. The compositions may be administered to a human patient, cat, dog, large animal, or an avian. The composition may be administered 1, 2, 3, 4, 5, 6, 7, 8, 9, 10, 11, or 12 times per day.

d. Formulation

The compositions provided herein may be in the form of capsules, sprinkle formulation, tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions provided herein may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions provided herein may also be formulated as suppositories, which may contain suppository bases including, but not limited to, cocoa butter or glycerides. Compositions provided herein may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions provided herein may also be formulated as transdermal formulations comprising aqueous or nonaqueous vehicles including, but not limited to, creams, ointments, lotions, pastes, medicated plaster, patch, or membrane.

Compositions provided herein may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions provided herein may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

The present invention has multiple aspects, illustrated by the following non-limiting examples.

Example 1

Treating PWS

This example shows how a $K_{ATP}$ channel opener addresses abnormalities observed in patients with PWS. In particular, the channel opener diazoxide may hyperpolarize hypothalamic neurons in a manner similar to leptin.

Diazoxide has now been prescribed at low doses for two infants with PWS, both of which had experienced hypoglycemic episodes. One infant in PWS nutritional phase 1a transitioning to phase 1b was started at 0.5 mg/kg BID of diazoxide at eight months of age, increasing to 1 mg/kg BID. No changes in blood pressure or heart rate were observed, and no signs of edema were present. Within two weeks of starting diazoxide, the infant's strong narcoleptic response to solid foods had been virtually eliminated. Subjectively, her energy level and stamina also improved, and her therapists documented her significant progress. The infant's baseline IGF-1 levels were 152 ng/mL while on 0.8 mg QD of Genotropin. Around three weeks after starting diazoxide levels, the IGF-1 levels had risen to 185 ng/ml, and the Genotropin was reduced to 0.6 mg QD with no decline in energy level. Two and half weeks later, despite the decline in growth hormone dosage, the patient's IGF-1 levels had continued to rise to 210 ng/ml. A significant increase in smiling over this period was noted. This child has not progressed to PWS nutritional phase 2a for a period of 56 weeks, perhaps as a result of the administration of diazoxide.

The second infant in PWS nutritional phase 1a was treated with 1 mg/kg BID of diazoxide. This infant also had experienced excessive fatigue while feeding and was reliant on a g-tube prior to initiating the medication. Following initiation of diazoxide, the infant was feeding exclusively by mouth, transitioning to nutritional phase 1b. It was further reported that the infant was more aware of his environment and was making more eye contact. His IGF-1 levels also rose while on a stable dose of growth hormone, with similar improvements in energy and stamina noted.

With respect to safety, no side effects have been reported for a period of 56 weeks. Both infants' blood sugar levels were monitored and were in the normal range. Minimal or no excess lanugo hair growth had been noted. Taken together, these cases are supportive of the utility of diazoxide in the treatment of PWS.

I claim:

1. In a method of treating a Prader-Willi Syndrome (PWS) patient with a diet having restricted or reduced caloric intake compared to the recommended daily allowance (RDA), the improvement comprising administering to the PWS patient diazoxide or a salt thereof in an amount effective to reduce one or more food-related behavioral symptoms.

* * * * *